(12) United States Patent
Arya

(10) Patent No.: US 6,941,697 B2
(45) Date of Patent: Sep. 13, 2005

(54) COILED FUMIGANT SET

(76) Inventor: Bimal Arya, D-944, New Friends Colony, New Delhi (IN), 110065

( * ) Notice: Subject to any disclaimer, the term of this patent is extended or adjusted under 35 U.S.C. 154(b) by 57 days.

(21) Appl. No.: 10/472,560
(22) PCT Filed: Mar. 28, 2001
(86) PCT No.: PCT/IN01/00054
§ 371 (c)(1),
(2), (4) Date: Jan. 22, 2004
(87) PCT Pub. No.: WO02/076201
PCT Pub. Date: Oct. 3, 2002

(65) Prior Publication Data
US 2004/0111954 A1 Jun. 17, 2004

(30) Foreign Application Priority Data
Mar. 23, 2001 (IN) .......................................... 345/Del/2001

(51) Int. Cl.⁷ .............................................. A01M 13/00
(52) U.S. Cl. ........................................................ 43/124
(58) Field of Search .......................... 43/124, 125, 127, 43/129; D22/122

(56) References Cited

U.S. PATENT DOCUMENTS

| | | | | |
|---|---|---|---|---|
| 3,754,861 A | * | 8/1973 | Sadahiro | 422/126 |
| 3,795,999 A | * | 3/1974 | Tabita | 43/127 |
| 5,657,574 A | * | 8/1997 | Kandathil et al. | 43/125 |
| 6,389,739 B1 | * | 5/2002 | Borut et al. | 43/125 |
| 6,406,673 B1 | * | 6/2002 | Soller et al. | 422/126 |
| 6,419,898 B1 | * | 7/2002 | Flashinski et al. | 424/40 |

* cited by examiner

Primary Examiner—Teri Pham Luu
Assistant Examiner—Bethany L. Griles
(74) Attorney, Agent, or Firm—Nath & Associates PLLC; Harold L. Novick

(57) ABSTRACT

The invention provides an improved coil fumigant set substantially quadrilateral in shape, comprising 2 or 4 coil members, wherein, each member integrated with the other member(s), each member has a central eye-piece and a runner, and the eye-pieces of the members are disposed at 180° or 90° with respect to one another to form a matrix of two coil members or four coil members and wherein, the runner of each coil member runs substantially parallel to the runners of the other member(s) and the runners run substantially in the form of a quadrilateral, with the corners of the quadrilateral being less than 90° and the radii decrease progressively towards the central eye-piece.

11 Claims, 6 Drawing Sheets

COILED FUMIGANT SET

TECHNICAL FIELD

The invention relates to an improved coiled fiumgant set, substantially quadrilateral in shape and a method for the manufacture of the said fumigant set. More particularly the invention relates to a matrix capable of accommodating 2 or 4 coil members for use as incense and/or insecticidal device.

BACKGROUND ART

Fumigants are commonly used to ward to off insects or to provides fragrance/aroma to the atmospheres/environment in dwellings. Most of these articles comprise an active ingredient dispersed in burning material. For instance, if the article is intended to act as a household insecticide, the active ingredient is an appropriate synthetic and/or natural insecticide that is released in the atmosphere and emits fumes which repel insects. Similarly, if the purpose of manufacture is to use the articles as air-freshening devices, the active ingredients are synthetic or natural fragrances or the admixtures thereof that evaporate on burning and emit pleasant fragrances. Such agents, may be for example, sandalwood powder or essential oils obtained from aromatic plants. The commonly used active ingredients in case, the fumigant is to function as a domestic and or outdoor insecticides are (S-2-Methyl-4-oxo-3-(2-propynyl) cyclopent-2-enyl(1)-cis.transchrysanthemate (common name: Prallethrin; brand name: Etoc, product of Sumitomo Chemical Co., Ltd.,), d-allethrin (brand name Pynamin Forte, product of Aventis Crop Science), Esbiothrins (trade name EBT product of Aventis Crop Science), Transfluthrin (common name and product of Bayer, Germany) and/or synthetic pyrethroids or other similar active ingredients combined with burning materials such as coconut shell powder, saw dust, binding agents, starch, etc. Aids that sustain burning of the article for a long period are also added optionally.

U.S. Pat. No. 4,144,318 describes a mosquito coil composition containing 72–83% by weight based on dry ingredients of a carrier selected from sawdust, coconut shell etc 16–26% by weight potato starch, water etc. The prior art is replete with compositions useful as insect repellents or as incense materials.

U.S. Pat. No. 3,819,823 discloses a mosquito coil containing a chrysanthemic acid ester. Another insecticide is disclosed in JP 58096004A2 containing substituted acetic acid ester. Thus, the prior art is replete with instances of insect repellent compositions used in coils. There is very little focus on the shape of the coils.

The earliest insect repellents are spiral coils such as illustrated in Japanese Patent 78027-341. This patent provides spiral coils which are produced from dough compositions of fibrous waste (such as rayon waste, cotton waste, mineral fibres etc).

U.S. Pat. No. 5,657,574 discloses a coiled insect fiumgant having enlarged outer portion for Providing quick coverage of an insect control ingredient in a space that previously resistance and kerosene and peanut shell powder to improve igniting and burning characteristics. This insect fumigant coil comprises radially outward, insect control ingredient-containing region linked to an insect control ingredient-containing inner coil, the inner coil extending radially inward from the radially outward region.

U.S. Pat. No. 4,765,090 describes self-supported mosquito incense formed with a plurality of lower extensions on the bottom surface of the incense coil and a plurality of upper recess portions on the upper surface of the coil wherein each lower extension is projectively corresponding to each upper recess portion, so that each upper coil can be overlapped on each lower coil for its handling or storage, and each coil can stably stand on any place or dish for smooth is burning without the aid of any teeth-supported ash tray.

U.S. Pat. No. 5,447,713 provides a mosquito coil in the form of a spiral which is punched out from a board consisting of wood-chip and/or wood-fiber material.

Another Japanese Patent Application 08168669 dated 10th Jun., 1996 and published on 22, Dec. 1997 discloses a mosquito repellent incense and a device for controlling the combustion time thereof. The application also provides a device for controlling the combustion time capable of freely setting the combustion time. Another problem with this type of coil is that its shape makes the coil prone to breakage and therefore does not lend itself to prolonged use.

GB Patent no 2139498 discloses an insect repellent device comprising a flexible backing sheet onto which is printed an elongated single continuous band or coil of material comprising a mixture of filler and active ingredient.

It is common knowledge that the common spiral coil is not structurally stable and is susceptible to breakage. Another problem associated with spiral coils is that once two or three coils are integrated or coupled as a set, it is quite difficult to separate the member coils without any breakage. Broken fragments of the coil are not preferred as the burning time of these fragments is very limited and difficult to fix at a suitable place for burning. Therefore, structural integrity of the formed coil is very important as the coil, in its final structure, should be provided a shape such that the coil is not prone to breakages on packaging, shipping or use. Therefore, there is a need in a prior art to improve the shape of the existing coils. The prior art at best teaches formation of spiral coils wherein two or three coils are integrated as a set. However, there is no teaching of a set comprising more than 3 coils in a set, such as a set of four coils.

Thus, there is a long felt need to improve the configuration of the coil set to provide improved stability and improved functions. It is to fulfil this long felt need that the applicant has developed novel coiled fumigant set, substantially quadrilateral in shape.

OBJECTS OF THE INVENTION

Accordingly, the main objective of the invention is to provide an improved coiled fumigant set, substantially quadrilateral in shape, capable of being used as an incense and/or insect-repellent, Another object is to provide a coiled fumigant set having either two or four coil members. Yet another object of the invention is to provide an improved fumigant with high integrity of shape and excellent dimensional stability.

Still another object of the invention relates to a fumigant coil set wherein each coil member has a runner which runs substantially parallel to the runners of the other coil members.

Yet another object is to provide an improved coiled fumigant set having a cloning design that can accommodate the integration of four coil members.

Still another object is to provide a quick method for manufacture of large number of coils at a time.

One more object of the invention relates to a coil set having improved functions.

A further object is to provide an improved coil set having improved configuration.

SUMMARY OF THE INVENTION

Accordingly, the invention provides an improved coiled fumigant set having substantially quadrilateral shape and having one, two or four coil members. The invention also provides a method for manufacture of coils in large numbers.

DETAILED DESCRIPTION OF THE INVENTION

Accordingly, the invention provides an improved coil fumigant set substantially quadrilateral in shape, comprising 2 or 4 coil members, wherein, each member integrated with the other member(s), each member has a central eye-piece and a runner, and the eyepieces of the members are disposed at 180° or 90° with respectively to one another to form a matrix of two coil members or four coil members and wherein, the runner of each coil member runs substantially parallel to the runners of the other member(s) and the runners run substantially in the form of a quadrilateral, with the corners of the quadrilateral being less than 90° and the radii decrease progressively towards the central eye-piece.

In an embodiment, the runners of the coil members run parallel to one another so as to impart a substantially quadrilateral shape to the coil set.

In yet another embodiment, the runners complete 2 to 6 windings around the eye-piece. In still another embodiment, a substantially quadrilateral-shaped coil, said coil comprising a central eye-piece twisted at 90° and a runner winding into quadrilaterals around the center, the edges of each coil being rounded off and each side of each coil being placed at about 90° from the other.

In yet another embodiment, comprising two to four coils being cloned into each other to form an integrated coil.

In still another embodiment, the coil set comprises four members integrated with each other wherein, the eye-pieces of each member is disposed at 90° with respect to each other and runners of each member run substantially parallel to each other in the form of a quadrilateral, with the edges rounded off.

In still another embodiment, the coil set comprises two members integrated with each other wherein, the eye-pieces of each member is disposed at 180° with respect to each other and runners of each member run substantially parallel to each other in the form of a quadrilateral, with the edges rounded off.

In yet another embodiment, the runners run substantially to each other and the width of the runners as well as the depth of the runners are varied.

In yet another embodiment, the depth of the coil may be increased to the extent desired.

In still another embodiment, a gap between the runners is 0.2 mm to 1.5 mm.

In yet another embodiment, the runner of the coil member has a width of 3 to 8 mm.

In one more embodiment, the runner of the coil member has a breadth of 2 to 8 mm.

In another embodiment, the width of the two set coil member is more than the depth of the member.

In still another the width of the four set coil member is less than the depth of the member.

In yet another embodiment, the width of the two set coil member is more than the depth of the member.

Accordingly, the invention provides an improved coiled fumigant set having substantially quadrilateral shape. The applicant has found to his surprise that fumigant coils that have substantially quadrilateral shape, in particular squarish in shape, have high structural integrity. This structural integrity of the coil is attributed to the unique configuration imparted to the coil.

For better understanding, the invention has been illustrated by the following accompanying drawings wherein.

Figure 1:
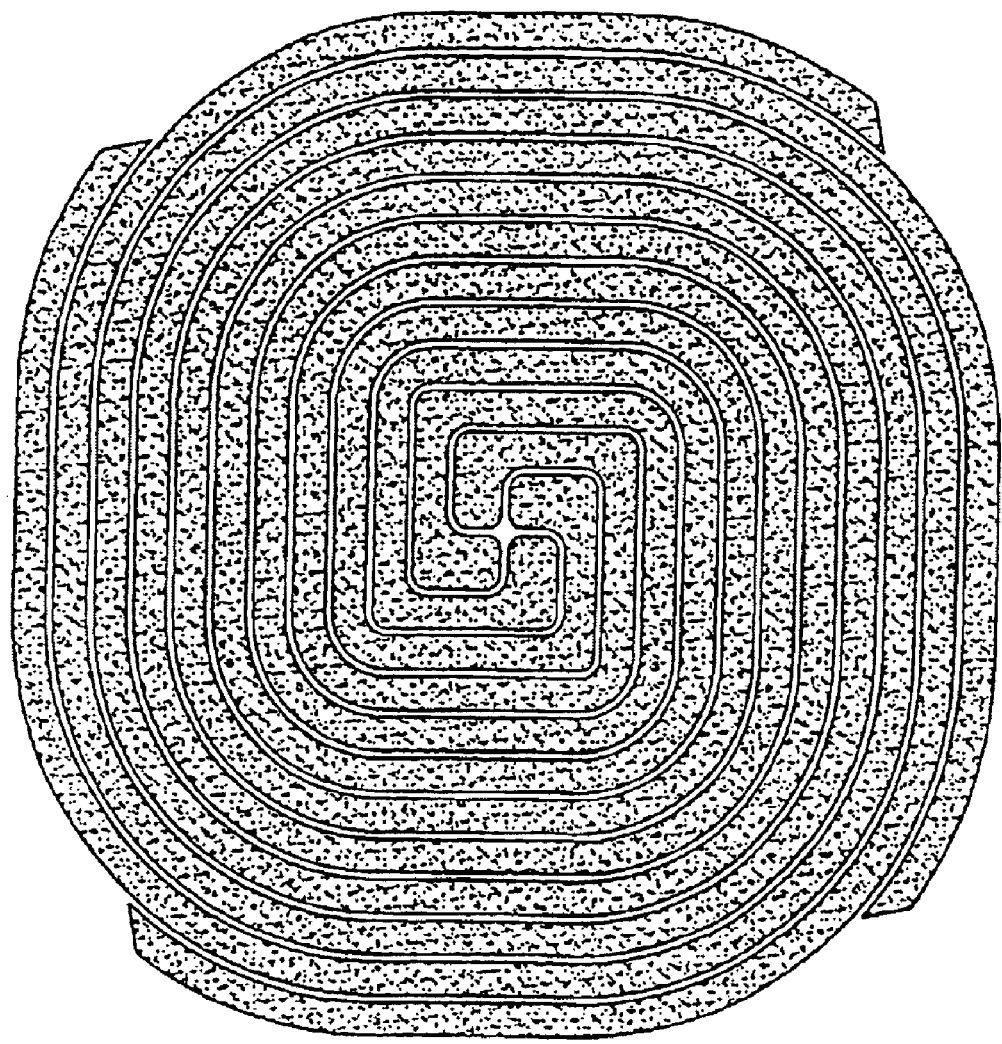
FIG. 1 represents an improved coiled fumigant set having four members.
Figure 2:
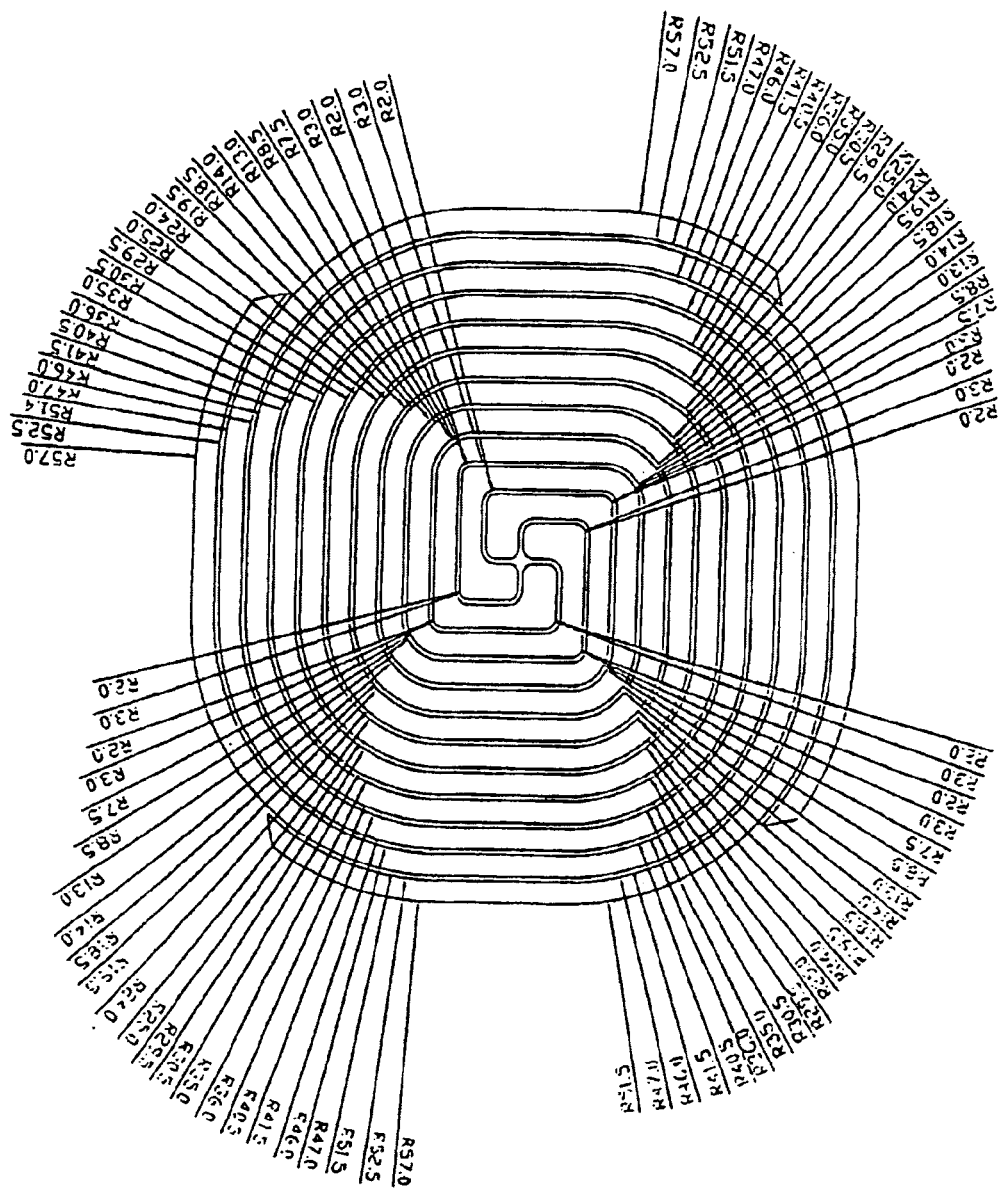
FIG. 2 represents the radii formed at the edges of the fumigant set of four coil members
Figure 3:
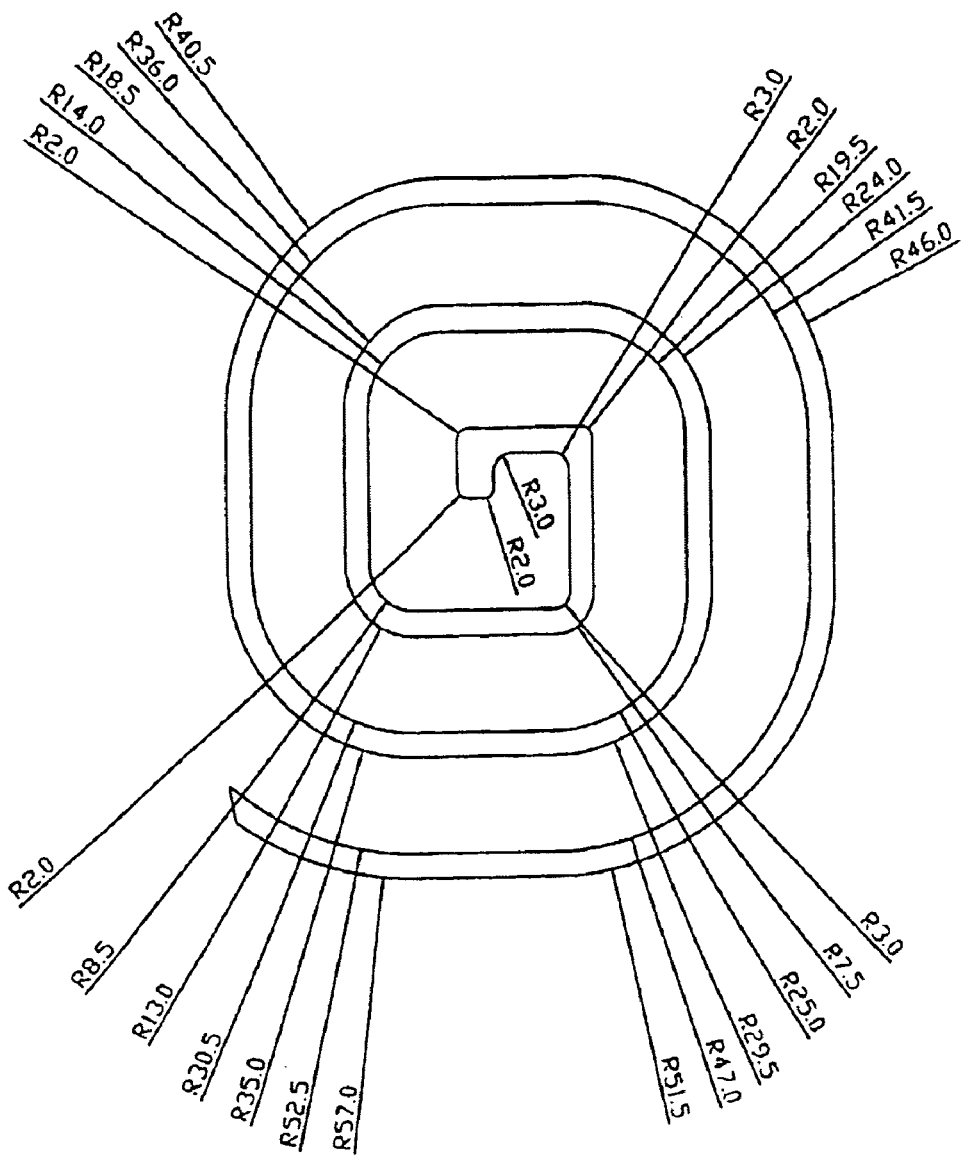
FIG. 3 represents the inner and outer radii of the edges of the individual member coil in a four coil set
Figure 4:
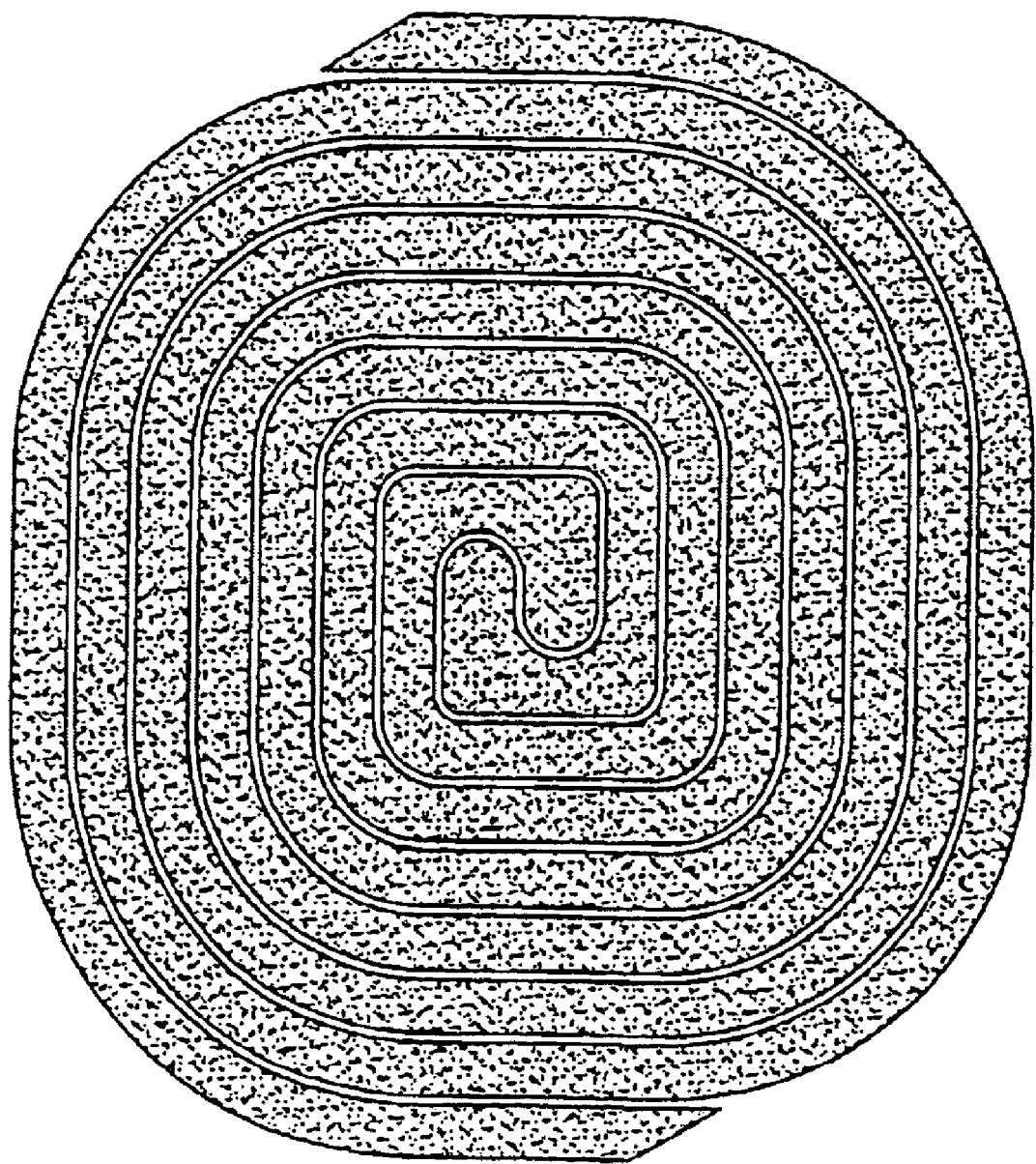
FIG. 4 represents the planar view of a coiled fumigant set comprising two members.
Figure 5:
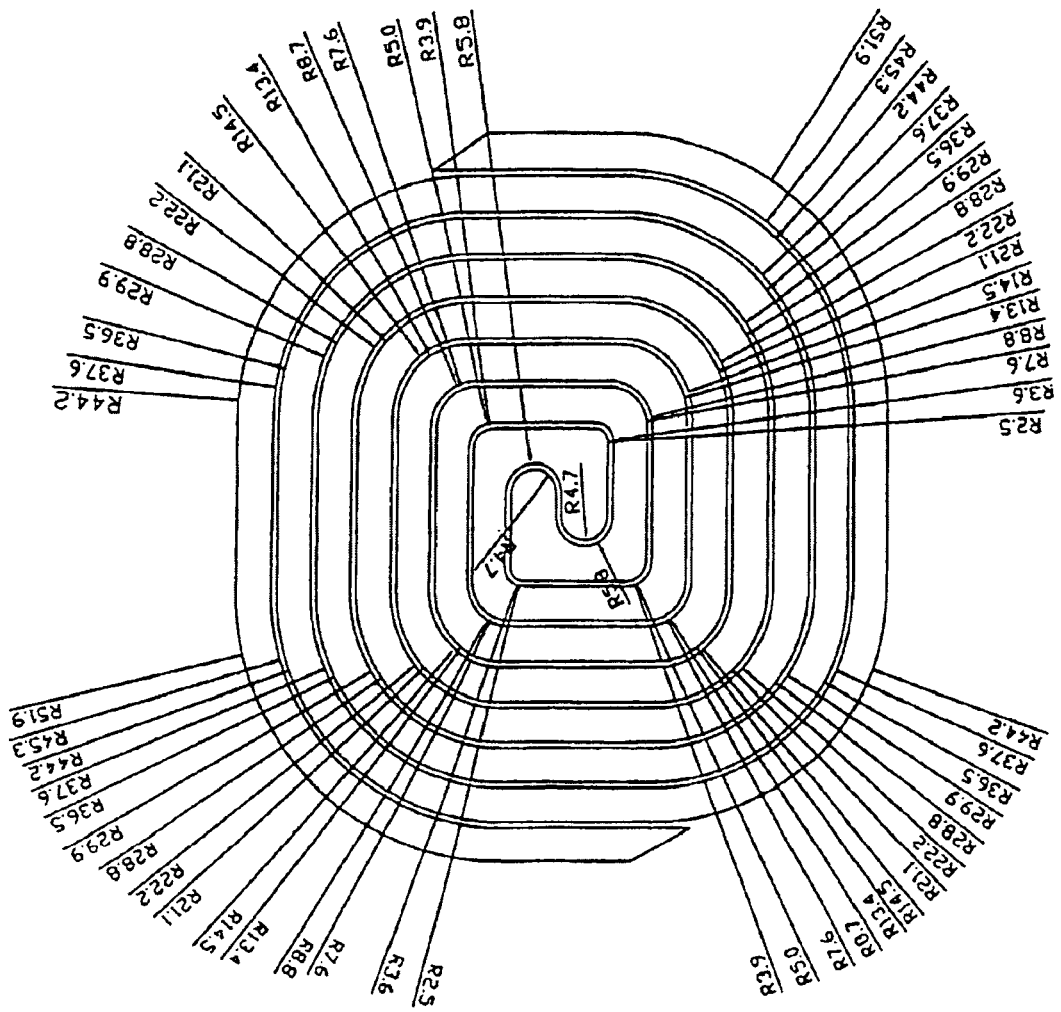
Figure 6:
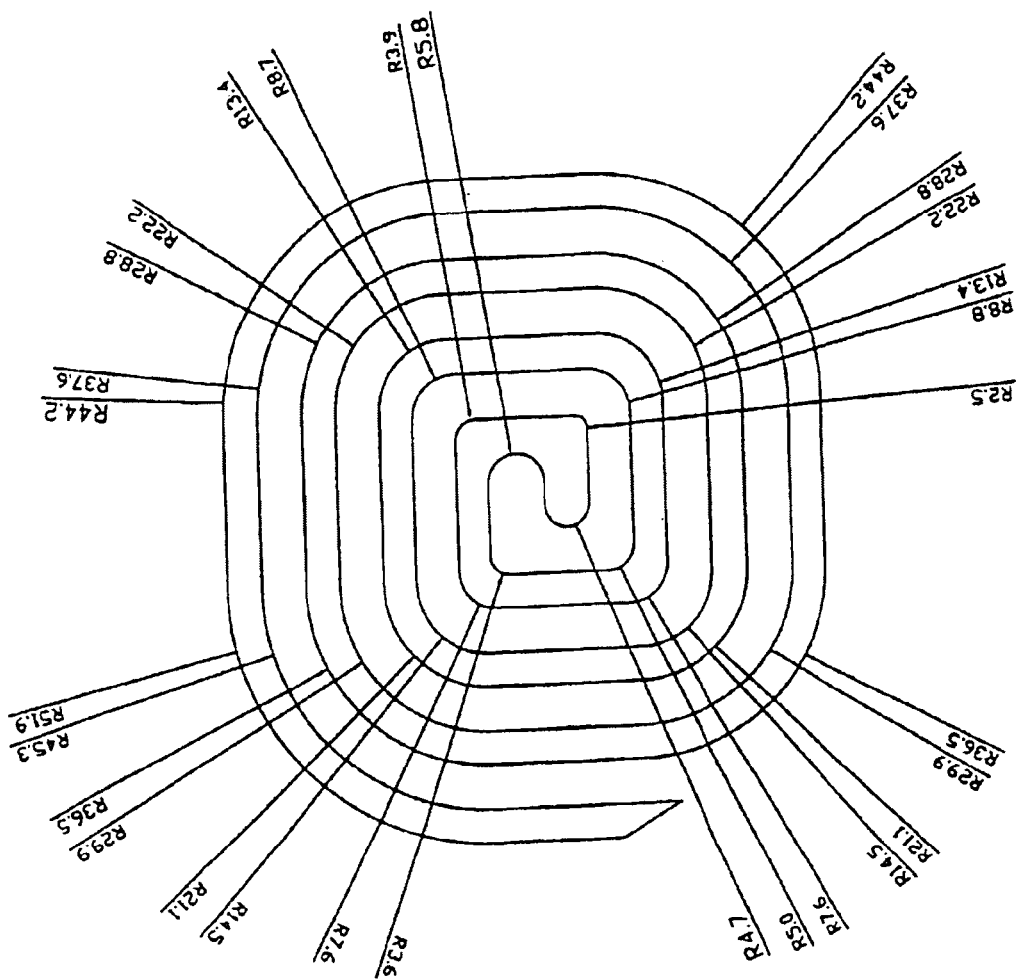

FIG. 5 represents the radii formed at the edges of the fumigant set of two coils FIG. 6 represents the inner and outer radii of the edges of the individual member coil in a two coil set The improved coiled fumigant set of the invention may be composed of conventional active ingredients combined with appropriate additives and binding agents. These materials are mixed by processes known in the art and punched out of an appropriate mould. While the composition of the coil may have its own contribution to the integrity of the coil, the novelty of this invention lies in the unique quadrilateral shape imparted to coils FIG. 1 shows a preferred coiled fumigant set of the invention, comprising four individual member coils. Each member coil has a central eye-piece (1) and a runner(2). When four member coils are integrated as a set, the eye-pieces of each member coil are disposed at 90° with respect to each other. Each of the eye-pieces are bent at about 90° so as to assume the shape of "L". The runners of the member coils emerging from the respective eyepieces, run substantially parallel to each other in the shape of a continuing quadrilateral and extend radially outward. The runners thus form two or more windings/coils around the central eye-piece and extend radially outwards. The edges of the quadrilateral are rounded off at varying radii which increase progressively from the center to the outward edge as shown in FIGS. 1 to 6. This construction imparts a substantially quadrilateral shape to the coiled fumigant set.

Another interesting feature of the improved coiled fumigant set is that the runners of the individual member coils ran substantially parallel to each other and maintain a constant distance between each other. This distance between the runners of the coils may be about 0.2 to 1.5 mm. This distance may be varied depending on the thickness of the coils and the number of member coils intended to be integrated.

There is no hard and fast rule to determining the size of the fumigant set and the other parameters of the coil members; these are varied by each manufacturer depending on the commercial and process requirements. In general, it is recommended that the thickness of the coil may range from 2 to 8 mm and the depth of the coil may at best be 3 to 8 mm. A notable feature is that in case of a set of two coils, the width of the runner of the coil member may be more than its depth; whereas, in case of a 4 member coil set, the width is less than the depth. The dimensions prescribed herein need not be strictly followed, but are recommended to achieve best results.

Yet another feature of the improved coiled fumigant set is that the runners are provided with markers or connectors at the edges. The function of these connectors is to keep the individual member coils in firm grip. When the coiled fumigant set is tapped lightly, the connectors release the runners immediately in contact, thus allowing the member coils to be easily separated.

The unique geometry of the coil i.e the quadrilateral shape imparted to the coil set has certain advantages giving this type of coils an edge over the conventional spiral coils. Some of these advantages are enlisted hereunder:

1. Dimensional and Structural Stability:

It is found that coils of quadrilateral shape, especially of the shape of a square are less prone to breakage than conventional spiral coils. The matrix with four coil members provides an extensive and uneven surface area. As a result, when the coiled fiumgant set is dropped to the floor from a certain height, the matrix of coils of the invention is found to be intact as compared to coils made having the same composition, but having conventional spiral shape. The reason for the coils of the invention being less prone to breakage than coils of other shapes is attributed to the quadrilateral shape of the matrix which is capable of offering greater resistance to the impacting forces.

To prove this aspect, the applicant conducted a drop-test wherein coils of the same composition were made in a quadrilateral shape according to the invention as well as in the conventional spiral form. It was found that coils of quadrilateral shape were less prone to breakage than spiral coils. The results of the tests are depicted in Table 1.

2. Maximum Integration of Coils

It is known that two spiral member coils may be integrated and sold as a set. According to WO 97/42814, three member coils may be integrated in a set. However, there is no teaching in the prior art that enables the manufacture of four member coils as a set. The applicant has found that when the member coils are imparted a substantially quadrilateral shape, the eye-pieces may be so disposed with respect to each other (at 90° in case of a matrix of four, or 180° in case of a matrix of two), that a maximum of four member coils may be integrated as a set. This is possible exclusively on account of the unique geometry (quadrilateral shape) imparted to the coiled fumigant of the invention. The tensile strength of the coil was assessed by a test wherein the edge/tip of the coil and the eye-piece were pulled until the coil gave away and broke. The results of the test are shown in Table 2. The results show that the coils of quadrilateral shape have more strength than spiral coils.

3. Easy Separability

The applicant has found to his surprise that the coiled fumigant set of the invention may contain even four members in a set, but the presence of these four members does not hamper the separability of the member coils. In fact, it is found that each of the member coils can be separated from each other easily without much effort. Further, to retain or protect the structure-cum-shape of the member coils, connectors are provided at the corners of the quadrilateral, at the time of drying of the coil (during the process of manufacture). These connectors are minute accumulations of the composition that hold the runners of the members of the coil set firmly and at the same time enable easy separation of the member coils. The applicant also believes that the quadrangular shape of the coiled fumigant set allows sufficient room and air space between the member coils (their runners) so that a gentle tap sets the member coils free from each other.

4. Long Burn Time:

Generally, the active ingredient (insecticide, insect repellent etc) is dispersed in a composition of burning materials. This composition is extruded on a conveyor belt and the coils of desired shape are punched out When the coil burns, the part of the coil that is ignited, probably has no or substantially less amount of active ingredient. The part of the coil immediately adjacent to the ignited portion is very hot. The active ingredient residing at this part, evaporates, on account of the heat. The smoke/fumes generated by the burning of the residue material of the coil keeps the active ingredient in circulation in the atmosphere.

It is found that although spiral coils claim to have a burn time of 8 hours, they tend to burn for less than seven hours at a stretch. This is true of a single member coil of spiral shape. The Applicant has found that coils of quadrilateral shape tend to burn for a longer period than conventional spiral coils. The applicant believes that the quadrilateral shape of the coil is critical in regulating the burn time of the coil. Coils of quadrilateral shape are provided with radii less than 90 degrees (as shown in FIGS. 1 to 6). In other words, the edges of the quadrilateral are rounded off. The coil at first commences and proceeds burning at a regular speed as long as the runners lie in the arms of the quadrilateral. Once the edge is approached, at which the runners at a specific radii, turn to form another arm of the quadrilateral, the speed of burning no longer remains constant It is interesting to note that at these radii/these edges, the coil is forced to bend at a particular angle. The occurrence of this bend at this and other similar sites, brings down the speed at which the coil is burning. Since in a quadrilateral, these bends occur frequently, the speed of burning of the coil is highly regulated and therefore, the member coil, on the whole has a longer burn time than conventional spiral coils.

5. Ability to Manufacture Large Number of Coils

Yet another advantage conferred by the unique shape of the coil is that a large number of can be manufactured at a time as compared to the rate of manufacture of spiral coils. As is known in the art, a board is first manufactured employing the desired composition. Sets of coils of the desired shape are punched out from this board. The sets of coils are punched out successively, for example, in a row. In case of a spiral coil, the first disadvantage is that only two coils can be punched out at a time. Secondly, the spiral shape of the coil itself poses a limitation in that, although the coils may be punched out as sets successively, huge amount of board material is wasted. As opposed to this, the quadrilateral shape allows the manufacturer to punch out a set comprising four member coils at a time. Further, the amount of board material used to produce such coils is less as compared to spiral coils. This improves the production process and saves cost and other balancing equipment in the production line.

TABLE 1

Comparision results for Quadrilateral and Round Fumigant Coil Sets punched from extruded belt of identical formulation
Round Coils

|  | Weight gms | Moisture % age | Thickness mm | Breakability kgs | Tensile gms | Burntime hours |
|---|---|---|---|---|---|---|
| MIN | 24.00 | 8.60 | 3.87 | 1.70 | 130.00 | 6.31 |
| MAX | 24.60 | 9.00 | 4.00 | 3.10 | 200.00 | 7.07 |
| AVG | 24.45 | 8.79 | 3.95 | 2.26 | 164.20 | 6.42 |

Drop test breakage in percents - 16%

TABLE 2

| | Quadrilateral Coil | | | | | |
|---|---|---|---|---|---|---|
| | Weight | Moisture | Thickness | Breakability | Tensile | Burntime |
| MIN | 24.3 | 8.4 | 3.89 | 2 | 195 | 7.18 |
| MAX | 24.9 | 8.8 | 4.02 | 2.42 | 230 | 7.3 |
| AVG | 24.62 | 8.66 | 3.94 | 2.12 | 217.5 | 7.24 |

Drop test breakage in percents - 8%

What is claimed is:

1. An improved coil fumigant set substantially quadrilateral in shape, comprising
    4 coil members, wherein each member is integrated with the other members,
    each member has
        an eye-piece, and the eyepiece of each member is disposed at 90° with respect to one another around a central point to form a matrix of four coil members and,
        a runner, the runner of each coil member has a constant width of between 3 mm and 8 mm and runs substantially parallel to the runners of the other members at a spacing between said runners of 0.2 mm to 1.5 mm, and the runners run substantially in the form of a quadrilateral, with the corners of the quadrilateral being less than 90° and the radii decrease progressively towards the central eye-piece.

2. A coil set as claimed in claim 1, wherein the runners complete 2 to 6 windings around the eye-pieces.

3. A coil sat as claimed in claim 1 wherein the radii at the corners of the quadrilateral may vary between 2 degrees to 57 degrees.

4. A coil set as claimed in claim 1, comprising four coils being caned into each other to form an integrated coil.

5. A coil set as claimed in claim 1, wherein the coil set comprises four members integrated with each other, the eye-pieces of each member is disposed at 90° with respect to each other and runners of each member run substantially parallel to each other in the form of a quadrilateral, with the edges rounded off.

6. A coil set as claimed in claim 1 wherein the runners run substantially to each other and the depth of the runners are varied.

7. A coil set as claimed in claim 6 wherein the depth of the coil may be increased to the extent desired.

8. A coil set as claimed in claim 1, wherein the runner of the coil member has a breadth of 2 to 8 mm.

9. A coil set as claimed in claim 1 wherein the width of the four set coil member is less than the depth of the member.

10. A coil set as claimed in claim 1 wherein the eye-piece has a means in the form of a slit or a cross at its center to facilitate attachment with a stand/holder.

11. A coiled insect fumigant consisting of a substantially quadrilateral-shaped coil, said coil comprising four coil members, each coil member having a central eye piece and a runner attached to said eye piece so as to form an L-shape, said four eye pieces disposed at 90 degrees with respect to one another at a center point of said coil, said runner winding into quadrilaterals around the center point, the edges of each coil member being rounded off and each side of each coil member being placed at about 90 degrees from the other.

* * * * *